United States Patent
Hartmann et al.

(10) Patent No.: US 10,744,108 B2
(45) Date of Patent: Aug. 18, 2020

(54) OMEGA-3 AND/OR OMEGA-6 FATTY ACID(S) IN IMPAIRED SPHINGOLIPID METABOLISM

(71) Applicant: K.D. PHARMA BEXBACH GMBH, Bexbach (DE)

(72) Inventors: Tobias Hartmann, Matzenbach (DE); Marcus Otto Walter Grimm, Homburg (DE); Thomas Floss, München (DE); Anke Wittmann, München (DE)

(73) Assignee: K.D. PHARMA BEXBACH GMBH, Bexbach (DE)

( * ) Notice: Subject to any disclaimer, the term of this patent is extended or adjusted under 35 U.S.C. 154(b) by 0 days.

(21) Appl. No.: 15/735,749

(22) PCT Filed: Jun. 10, 2016

(86) PCT No.: PCT/DE2016/100265
§ 371 (c)(1),
(2) Date: Dec. 12, 2017

(87) PCT Pub. No.: WO2016/198048
PCT Pub. Date: Dec. 15, 2016

(65) Prior Publication Data
US 2018/0214406 A1    Aug. 2, 2018

(30) Foreign Application Priority Data
Jun. 12, 2015   (DE) .......... 10 2015 109 352

(51) Int. Cl.
A61K 31/202 (2006.01)
C12Q 1/6883 (2018.01)
(52) U.S. Cl.
CPC .......... *A61K 31/202* (2013.01); *C12Q 1/6883* (2013.01)

(58) Field of Classification Search
CPC .......................... A61K 31/202; A61K 31/232
See application file for complete search history.

(56) References Cited

U.S. PATENT DOCUMENTS

2012/0252888 A1* 10/2012 Pantzaris et al. .... A61K 31/202
514/458

FOREIGN PATENT DOCUMENTS

EP       1419780      *  5/2004
WO    9966877  A2    12/1999
(Continued)

OTHER PUBLICATIONS

Berge et al., Journal of Pharmaceutical Sciences, 1977,66(1):1-19.*

*Primary Examiner* — San Ming R Hui
(74) *Attorney, Agent, or Firm* — Lucas & Mercanti, LLP; Klaus P. Stoffel (57) ABSTRACT

An application of omega-3 and/or omega-6 fatty acid(s) for the therapeutic treatment of the human or animal body in the case of an impaired sphingolipid metabolism, in particular in the case of impaired sphingolipid synthesis and/or excessive sphingolipid degradation. The agent is applied in the case of missing, reduced and/or defective formation of a sphingomyelin synthase enzyme in the body, in particular the enzyme sphingomyelin synthase 1 or the enzyme sphingomyelin synthase 2. The application has proved to be useful in the case of a defect of the sphingomyelin synthase 1 gene or of the sphingomyelin synthase 2 gene. The omega-3 and/or omega-6 fatty acid(s) preferably comprise(s) polyunsaturated omega-3 and/or omega-6 fatty acid(s), preferably EPA, DHA, DPA, ETA, 21:5n3 and/or SDA. A method for determining a cause of a disease in an animal or a human being and a device for carrying out the method are also provided.

20 Claims, 4 Drawing Sheets

(56) References Cited

FOREIGN PATENT DOCUMENTS

| WO | 0197802 A1 | 12/2001 | |
|---|---|---|---|
| WO | 2004056370 A1 | 7/2004 | |
| WO | WO-2004056370 A1 * | 7/2004 | ........... A61K 31/202 |
| WO | 2012103685 A1 | 8/2012 | |

* cited by examiner

| PC aa Species | wt (15 mice) | | | SMS1 Mutants (17 mice) | | | Significance | | Main fatty acids |
|---|---|---|---|---|---|---|---|---|---|
| | Intensity | % | SEM % | Intensity | % | SEM % | ttest | Significance | |
| PC aa total | 10,445,747 | 100.0 | 1.6 | 9,602,725 | 91.9 | 2.4 | 0.009 | ** | |
| PC aa saturated | 560,561 | 100.0 | 1.5 | 573,085 | 102.2 | 2.5 | 0.466 | | |
| PC aa unsaturated | 9,885,186 | 100.0 | 1.6 | 9,029,640 | 91.3 | 2.4 | 0.006 | ** | |
| PC aa CX:1 | 2,430,350 | 100.0 | 1.5 | 2,400,435 | 98.8 | 2.2 | 0.653 | | |
| PC aa CX:2 | 724,384 | 100.0 | 2.1 | 637,658 | 88.0 | 2.7 | 0.002 | ** | |
| PC aa CX:3 | 828,608 | 100.0 | 1.8 | 729,132 | 87.9 | 2.8 | 0.001 | *** | 20:5 20:4 22:5<br>18:0 18:1 16:0 |
| PC aa CX:4 | 2,744,306 | 100.0 | 1.7 | 2,572,597 | 93.7 | 2.3 | 0.035 | * | |
| PC aa CX:5 | 2,326,960 | 100.0 | 1.7 | 1,977,046 | 85.0 | 2.4 | 0.000 | *** | |
| PC aa CX:6 | 829,590 | 100.0 | 2.3 | 712,770 | 85.9 | 3.2 | 0.002 | ** | |
| PC aa C36:5 | 1,950,614 | 100.0 | 1.6 | 1,641,737 | 84.2 | 2.4 | 0.000 | *** | 22:6 22:5 20:5<br>20:4 18:1 18:2<br>16:0 18:1 |
| PC aa C34:1 | 1,798,063 | 100.0 | 1.3 | 1,786,490 | 99.4 | 2.1 | 0.797 | | |
| PC aa C36:4 | 1,618,575 | 100.0 | 1.4 | 1,506,247 | 93.1 | 2.4 | 0.021 | * | |
| PC aa C38:4 | 981,771 | 100.0 | 2.3 | 928,077 | 94.5 | 2.3 | 0.193 | | |
| PC aa C38:6 | 585,662 | 100.0 | 2.2 | 485,991 | 83.0 | 3.0 | 0.001 | *** | |
| PC aa C38:3 | 561,250 | 100.0 | 1.8 | 476,413 | 83.8 | 3.0 | 0.000 | *** | 18:1 18:2 |
| PC aa C36:1 | 456,553 | 100.0 | 2.9 | 458,581 | 100.4 | 3.4 | 0.922 | | |
| PC aa C32:0 | 380,136 | 100.0 | 1.4 | 407,912 | 107.3 | 2.7 | 0.026 | * | |

OMEGA-3 AND/OR OMEGA-6 FATTY ACID(S) IN IMPAIRED SPHINGOLIPID METABOLISM

The present application is a 371 of International application PCT/DE2016/100265, filed Jun. 10, 2016, which claims priority of DE 10 2015 109 352.9, filed Jun. 12, 2015, the priority of these applications is hereby claimed and these applications are incorporated herein by reference.

BACKGROUND OF THE INVENTION

The invention relates to an application of omega-3 and/or omega-6 fatty acid(s) and a method for determining a cause of a disease of an animal or a person and a device for performing the method.

Sphingolipids, in particular sphingomyelins, have various functions in cell membranes of mammals, which inter alia relate to the structure, adhesion and signal transmission of the cells and in particular also the cell nucleus. Consequently, diseases caused by a disequilibrium of the lipid composition can be caused by an impairment of the sphingolipid metabolism in the animal or human body.

SUMMARY AND DESCRIPTION OF THE INVENTION

The present invention is based on the problem of providing a means with which diseases caused by impaired sphingolipid metabolism can be treated.

According to the invention, this problem is solved by an application of omega-3 and/or omega-6 fatty acid(s) for the therapeutic treatment of the animal or human body in case of impaired sphingolipid metabolism.

Surprisingly it has been found that the impairment of the sphingolipid metabolism, i.e. in particular sphingolipid synthesis and the degradation of sphingolipids can at least to a certain extent be prevented or moderated by the application of the omega-3 and/or omega-6 fatty acid(s).

One explanation for this is that the composition of the sphingolipids, in particular the sphingomyelins, for example in the testis contains an exceptionally high percentage of long-chain, multiply unsaturated fatty acids such as omega-3 or omega-6 fatty acids, e.g. docosahexaenoic acid (DHA) and that therefore sources of such fatty acids must be present for sphingolipid synthesis. So that the content required for sphingolipid synthesis can be provided, on the one hand such fatty acids must be absorbed via the diet, and on the other hand short-chain fatty acids are converted into long-chain, multiply unsaturated fatty acids. If on the other hand these fatty acids are not provided in sufficient quantity, sphingolipid synthesis is impaired.

If, in spite of sources sufficiently abundant per se, the body does not provide a sufficient quantity of sphingolipids, the productivity of the sphingolipid synthesis can be increased through the application. One reason for this is that a greater production pressure exists when larger quantities of the omega-3 and omega-6 fatty acid(s) respectively are available.

If the impaired sphingolipid metabolism has the effect that the sphingolipids are degraded too rapidly in the body and for this reason are not available in sufficient quantity, this can be compensated by the application and the sphingolipid formation increased thereby.

Through the application of the omega-3 and/or omega-6 fatty acid(s), preferably by intravenous or oral administration, sufficiently large quantities of the long-chain, multiply unsaturated fatty acids are provided for utilization and the disease which is caused by the impaired sphingolipid metabolism can be cured or the symptoms caused by the disease can be moderated. Such a disease can include male infertility, storage diseases, dementia diseases, in particular Alzheimer's disease, Niemand-Pick disease or multiple sclerosis. Also possible as diseases are cancer diseases, Tay-Sachs disease, Sandhoff disease, Tay-Sachs AB variant, Gaucher disease, Fabry disease, Krabbe disease, GM1 gangliosidosis, metachromatic leukodystrophy and fucosidosis.

The sphingolipids and the gangliosides derived therefrom have an important function in particular in spermatogenesis. In cell membranes of sperms, phospholipids with multiply unsaturated fatty acids, in particular very long-chain sphingomyelins, form a major proportion of lipids. The inventors have discovered that a deficiency of the long-chain, multiply unsaturated fatty acids can lead to changes in spermatocytes and spermatids, in particular to defective maturation, and that the changes cause male infertility. It has surprisingly been found that not only can the occurrence of the changes be avoided through the application according to the invention, but also that already formed alterations regress again.

The application according to the invention is especially suitable for treatment in case of deficient, reduced and/or defective formation of a sphingomyelin synthase enzyme, in particular of sphingomyelin synthase 1 (SMS1) or/and sphingomyelin synthase 2 (SMS2) in the body. SMS1 and SMS2 catalyze de novo synthesis of sphingomyelin and diacylglycerol (DAG) from ceramides and phosphatidylcholines, while the homologous enzyme SMSr (sphingomyelin synthase-related) has no sphingomyelin synthase activity. SMS1 is positioned in the cis Golgi apparatus and is responsible for the formation of sphingomyelin. However, because of the vesicle-mediated substance exchange between the Golgi apparatus and plasma membranes, the highest concentration of sphingomyelin and other complex sphingolipids is present in the outer regions of the plasma membranes, in which the sphingolipid fulfil the functions described at the beginning. On the plasma membranes, these functions are mediated by SMS2, which plays an important part in the control of the ceramide levels of the plasma membranes.

Said scabbing disorders occur with impaired formation of SMS1 since SMS1 plays an important part in maintenance of the intracellular sphingomyelin homeostasis, which forms a sphingomyelin reserve, from which the plasma membranes are also supplied. A disequilibrium in the lipid metabolism which is caused by said impairment therefore affects the intracellular lipid composition and the lipid composition on the cell surface, which can alter protein transport, enzymatic activity and lipid-based cell signal transmission. Surprisingly, through the application according to the invention, the lipid metabolism can be brought back into equilibrium or at least closer to equilibrium.

The application has been found to be especially effective in case of a defect in the sphingomyelin synthase 1 gene and/or the sphingomyelin synthase 2 gene. The inventors have established that a defect in the respective gene leads to an age-dependent reduction in various long-chain, multiply unsaturated phosphatidylcholines, lyso-phosphatidylcholines and sphingolipids in the testis and can result in age-related infertility. Surprisingly, through the application of the omega-3 and/or omega-6 fatty acid(s), the effects of a defect in the sphingomyelin synthase 1 gene and/or the sphingomyelin synthase 2 gene can be compensated, so that said reduction no longer exists. Said changes regress through the application and the infertility can be cured.

In one configuration of the invention, the omega-3 and/or omega-6 fatty acid(s) comprise highly unsaturated omega-3 and/or omega-6 fatty acid(s), preferably EPA, DHA, DPA, ETA, 21:5n3 and/or SDA.

The omega-3 and/or omega-6 fatty acid(s) are advisedly used as free fatty acids or in bound form, in particular as esters or salts. Preferably, the agent is free from or low in fatty acids other than omega-3 and/or omega-6 fatty acid(s).

In one embodiment of the invention, the omega-3 and/or omega-6 fatty acid(s), especially in humans, are administered at a dosage of more than 0.5 g/day, preferably 1 to 3 g/day. Administration of 2 to 3 g/day has been found to be especially effective. On the other hand, administration of more than 5 g/day has been found to be inadvisable.

The omega-3 and/or omega-6 fatty acid(s) are preferably administered intravenously or orally. Preferably they are administered in the form of capsules, tablets or/and liquids. A certain dosage quantity of the agent is advisedly given one to three times, preferably twice per day. In an especially preferred embodiment of the invention, the omega-3 and/or omega-6 fatty acid(s) are obtained from fish, in particular fish oil, and/or microorganisms, in particular algae.

The initially mentioned method for determination of a cause of a disease of an animal or a person is characterized by an investigation of the sphingolipid metabolism of the animal or human body. As diseases possible causes whereof can be determined with the method, as stated above, in particular male infertility, but also storage diseases, dementia diseases, in particular Alzheimer's disease, Niemand-Pick disease or multiple sclerosis and in addition cancer diseases, Tay-Sachs disease, Sandhoff disease, Tay-Sachs AB variant, Gaucher disease, Fabry disease, Krabbe disease, GM1 gangliosidosis, metachromatic leukodystrophy and fucosidosis are possible. The investigation is advisedly performed in vitro.

In one configuration of the invention, a determination of the sphingolipids is performed, wherein preferably the content of sphingolipids present in the human or animal body is determined and/or a molecular structure and/or a composition of the sphingolipids in the human or animal body, is determined. Advisedly, the content of omega-3 and/or omega-6 fatty acid(s), preferably the content of EPA, DHA, DPA, ETA, 21:5n3 and/or SDA is determined.

In an especially preferred embodiment of the invention, the content of sphingolipids and/or the percentage of the sphingolipids which contain the omega-3 and/or omega-6 fatty acid(s), in particular EPA, DHA, DPA, ETA, 21:5n3 and/or SDA, is determined.

The determination is preferably performed in such a manner that the sphingolipids can be distinguished depending on the respective omega-3 and/or omega-6 fatty acid(s), in particular EPA, DHA, DPA, ETA, 21:5n3 and/or SDA, which they contain.

Alternatively or additionally, it is possible to investigate whether a gene defect, in particular a defect in the sphingomyelin synthase gene 1 and/or the sphingomyelin synthase gene 2, is present. Further relevant defects could relate to genes of the following enzymes, which could also be investigated: ceramidase (CDASE), ceramide kinase (CERK), ceramide synthase (CERS), ceramide transfer protein (CERT), dihydroceramide desaturase (DEGS), glucosyl ceramidase (GBA), 3-keto dihydrosphinganine reductase (KDSR), sphingomyelin synthase (SGMS), sphingosine 1-phosphate phosphatase (SGPP), sphingomyelin phosphodiesterase (SMPD), sphingosine kinase (SPHK), serine palmitoyl transferase (SPT) or/and UDP-glucose ceramide glucosyltransferase (UGCG).

The determination of the sphingolipids is advisedly performed in vitro on body fluid or/and body tissue of the human or animal body, preferably on blood, ejaculate, sperm and/or testicular tissue.

In a further configuration of the invention, on the basis of the sphingolipid content determined, the determined content of omega-3 and/or omega-6 fatty acid(s) or/and the content of sphingolipids and/or the percentage of the sphingolipids which contain omega-3 and/or omega-6 fatty acid(s), optionally taking account of body features of the person or the animal, for example size, body weight, body fat percentage or the like, it is determined whether a treatment of the disease by application of omega-3 and/or omega-6 fatty acid(s), in particular as described above or in claims 1 to 9, is indicated. In the determination, account can also be taken of how the omega-3 and/or omega-6 fatty acid(s) are constituted, wherein in particular the respective content of EPA, DHA, DPA, ETA, 21:5n3 and/or SDA can be determined.

In one embodiment of the invention, on the basis of the sphingolipid content determined, the determined content of omega-3 and/or omega-6 fatty acid(s) or/and the content of sphingolipids and/or the percentage of the sphingolipids which contain omega-3 and/or omega-6 fatty acid(s), a dosage suitable for the application of omega-3 and/or omega-6 fatty acid(s) for the treatment of the disease, preferably the dosage of EPA, DHA, DPA, ETA, 21:5n3 and/or SDA, or/and the content of EPA, DHA, DPA, ETA, 21:5n3 and/or SDA in a preparation to be taken in the context of the application, can be determined. During this, account is preferably taken of body features of the person or the animal, for example size, body weight, body fat percentage or the like.

For the analysis of the sphingolipids, in particular the sphingolipid content, the following are for example suitable:
  methods for thin layer chromatography, in particular 2D and HPTLC (high performance thin layer chromatography) methods, in particular for the determination of the content of sphingolipids,
  high performance liquid chromatography, in particular capillary HPLC (high performance liquid chromatography), for the determination of the content of sphingolipids, wherein a partial separation of the fatty acids can also be provided,
  methods for mass spectroscopy, preferably methods which are based on ESI (electron spray ionization) coupled with quadrupole, by means of which the individual lipid species of the sphingolipids can be detected and analyzed by MRM (multi-reaction monitoring), or/and
  gas chromatographic methods, in particular for analysis of the fatty acid composition of the individual sphingolipids.

For the analysis of the genes or enzymes as explained above, the following steps can be performed:
  isolation of the RNA, e.g. with Trizol,
  transcription of the RNA into cDNA by means of reverse transcriptase,
  insertion of restriction endonuclease cleavage sites by PCR (polymerase chain reaction),
  cloning into a plasmid,
  transformation of the plasmid into bacteria,
  isolation of the plasmid and
  sequencing of the plasmid.

For investigation of the promoter, an analogous method can be used, wherein the genomic DNA would be isolated instead of the RNA and this would then be amplified by PCR and cloned.

The device initially mentioned is intended for the determination of a cause of a disease of an animal or a person, in particular in case of male infertility, wherein it comprises a device for investigating the sphingolipid metabolism of the animal or human body. It is intended for performing the aforesaid method steps.

The investigation device advisedly comprises a device for thin layer chromatography, a device for high performance liquid chromatography, a mass spectrometer or/and a gas chromatograph.

In one configuration of the invention, the test device is devised for the determination of the sphingolipids in body fluid or/and body tissue of the human or animal body, preferably on blood, ejaculate, sperm and/or testicular tissue. The test device is advisedly provided for the determination of the sphingolipid content, the content of omega-3 and/or omega-6 fatty acid(s) or/and the content of sphingolipids and/or the proportion of the sphingolipids which contain omega-3 and/or omega-6 fatty acid(s).

In a further development of the invention, the device is devised for determining, on the basis of the determined sphingolipid content, the determined content of omega-3 and/or omega-6 fatty acid(s) or/and the content of sphingolipids and/or the percentage of the sphingolipids which contain the omega-3 and/or omega-6 fatty acid(s), optionally taking account of the body feature of the patient, for example size, body weight, body fat content or the like, to determine whether a treatment of the disease by use of omega-3 and/or omega-6 fatty acid(s), in particular as described above or in claims 1 to 9, is indicated.

In one embodiment of the invention, the device is provided for determining, on the basis of the determined sphingolipid content, the determined content of omega-3 and/or omega-6 fatty acid(s) or/and the content of sphingolipids and/or the percentage of the sphingolipids which contain omega-3 and/or omega-6 fatty acid(s), optionally taking account of body features of the human or the animal, for example size, body weight, body fat percentage or the like, a suitable dosage for the application of omega-3 and/or omega-6 fatty acid(s), preferably the dosage of EPA, DHA, DPA, ETA, 21:5n3 and/or SDA, or/and the content of EPA, DHA, DPA, ETA, 21:5n3 and/or SDA in a preparation to be taken in the context of the application.

Below, the action of the application is explained in more detail on the basis of examples and the appended tables, graphs and drawings, which relate to the examples:

EXAMPLES AND DETAILED DESCRIPTION OF THE INVENTION

Figure 1:
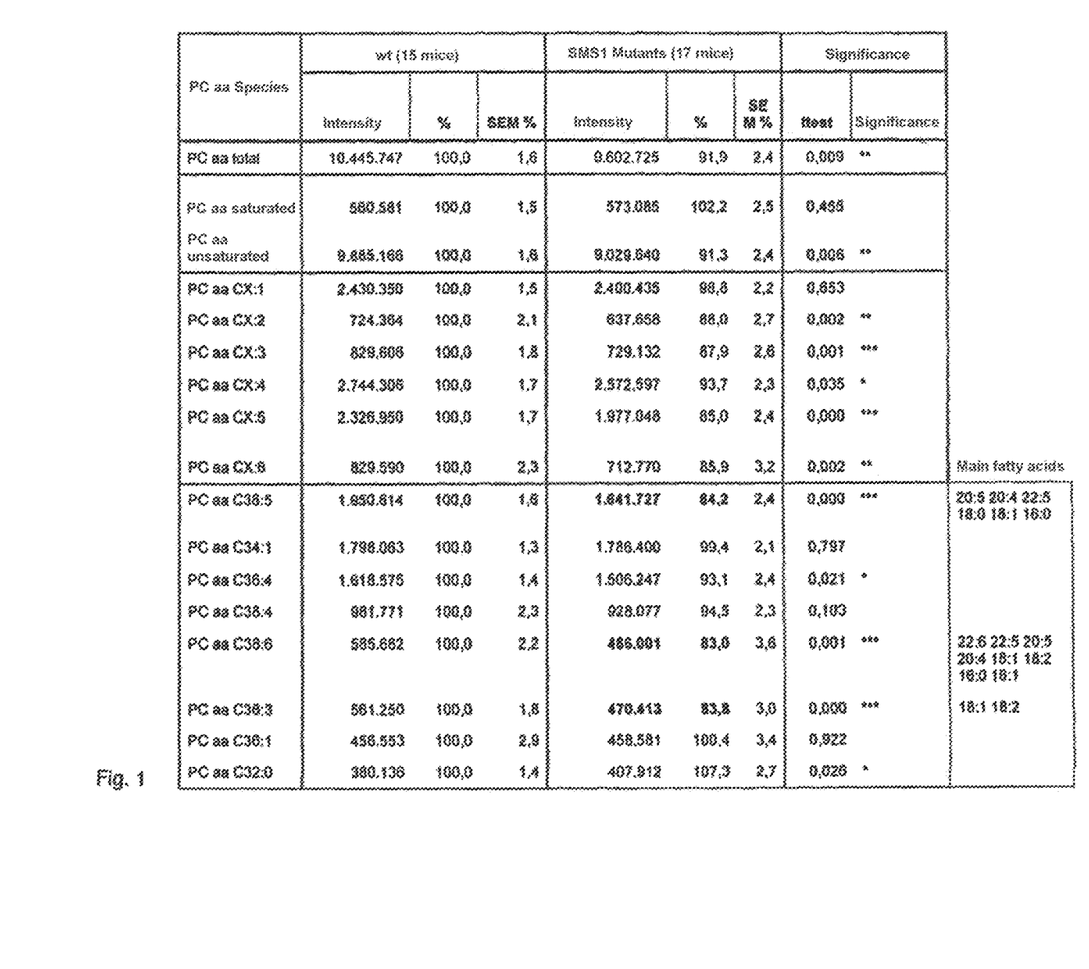
FIG. 1 shows a table with results of a mass spectrometric analysis of phosphatidylcholine fatty acids composition in testes of mice, FIG. 2 testicular phenotypes of mice, FIG. 3 a graph relating to the litter sizes of mice after mating, FIG. 4 a graph relating to the duration until the first litter of mice after mating, and FIG. 5 hematoxylin and eosin staining of the testes.

In mice of the C57Bl6J strain, the function of the sphingomyelin synthase 1 (SMS1) was completely or at least largely removed by means of the gene trap method corresponding to a knockout. These mice are referred to below as genetically modified mice. In comparison to a reference group of non-genetically manipulated mice of the C57Bl6J strain, which are referred to below as "wild type mice", this resulted in a decrease in sphingomyelin by 21.1% ($p<0.0001$) in the testis and in particular to a decrease in the percentage of multiply unsaturated fatty acids, in particular of multiply unsaturated omega-3 and omega-6 fatty acids. The decrease in the lipids and the fatty acids is not restricted to the sphingomyelins, but also relates to other phospholipids. As can be seen from the table in FIG. 1 inter alia, the decrease in phosphatidylcholine C38:6, which contains multiply unsaturated fatty acids such as DHA, EPA and arachidonic acid, was 17% ($p<0.001$).

Figure 2:
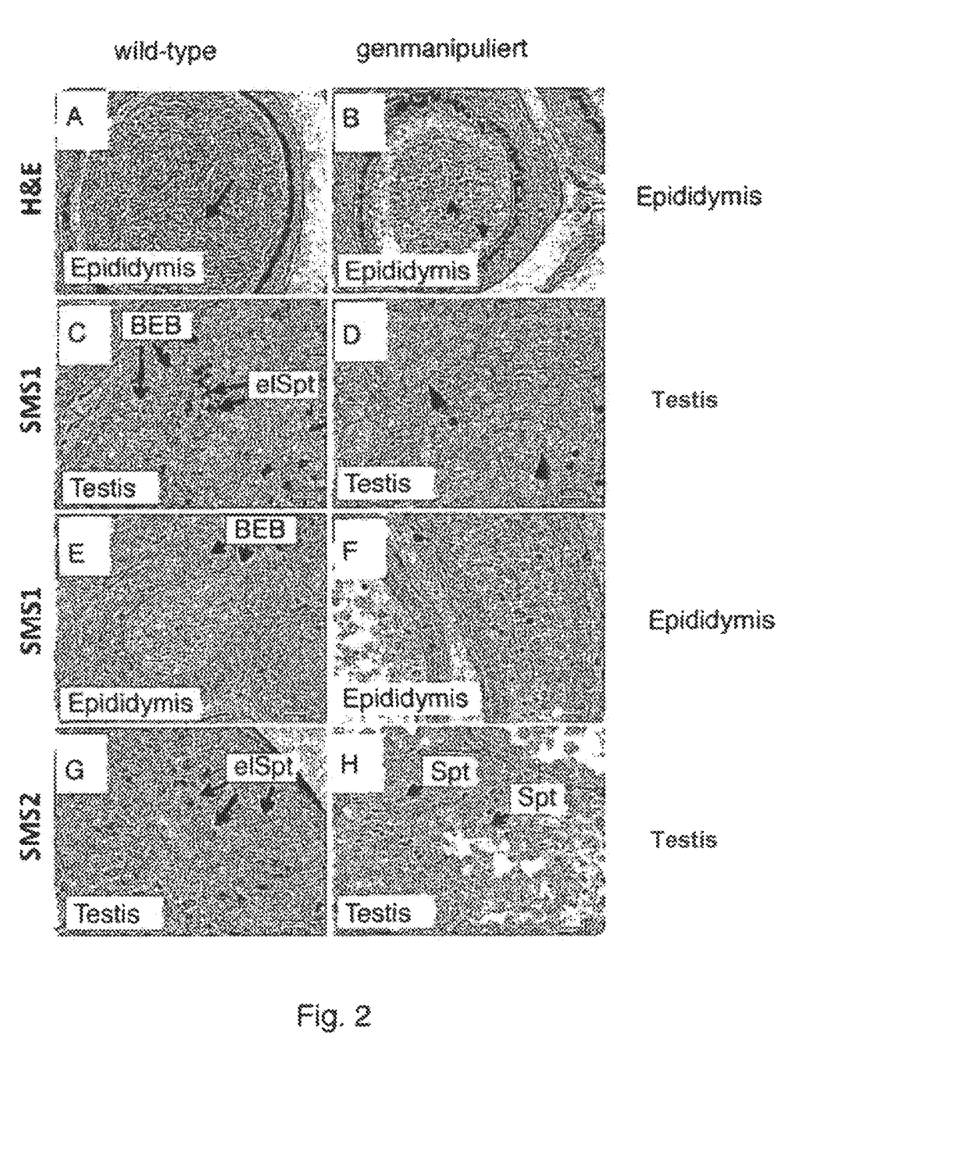

FIG. 2 shows pathological change in the testes of the genetically modified mice, which occurred in association with the decrease in the sphingomyelins. In FIGS. 2A and 2B show a hematoxylin and eosin staining (H&E staining) of testes of one of the wild type mice (FIG. 2A) and one of the genetically manipulated mice (FIG. 2B). The epididymides of the testes show an accumulation of changed cells in the genetically modified mouse (black arrowheads in FIG. 2B) relative to the mature spermatozoa of the wild type mouse (black arrows in FIG. 2A).

In the genetically modified mice (FIG. 2D), immunohistochemistry shows developing spermatocytes close to the intracellular space including the blood-testis barrier (BTB) and in acrosomes. Arrowheads in FIG. 2D point to large vacuoles within tubes in the genetically modified mouse, which reflect an especially strongly marked phenotype.

In immunohistochemistry, FIGS. 2E and 2F show SMS1 expression in cells which represent the major part of the epithelium. The comparison between the wild type mouse (FIG. 2E) and the genetically modified mouse (FIG. 2F) shows that the SMS1 expression is almost completely lacking in the genetically modified mouse.

As can be seen from FIGS. 2G and 2H, the immunohistochemistry for SMS2 is normally distributed in the wild type mouse, but in the genetically modified mouse it is at some points reduced to spermatid cells.

As a consequence of the altered sphingolipid metabolism and the defective lipid composition and testicular pathology derived therefrom, infertility occurred in male mice.

Firstly, the fertility of male wild type, heterozygotic and genetically manipulated mice was investigated by mating male mice with an 11-week old female mouse of the C57Bl/6J strain. The results of this study can be found in the graph in FIG. 3 on the basis of litter sizes achieved under Sms1WT (mating of the wild type mice), Sms1HET (mating of the heterozygotic mice) and Sms1MUT (mating of the genetically manipulated mice), each indicated by "−". After this study, the animals were regularly fed manually with a mixture of DHA/EPA (mixture of ethyl ester mixture with DHA (38%) and EPA (46), 9 mg per mouse daily). Male wild type mice, heterozygotic and genetically manipulated mice whose fertility had previously been studied were again mated for 13 weeks and were also further fed with DHA/EPA during this. The results of the second mating are each indicated by "+" in the graph in FIG. 3.

Figure 3:
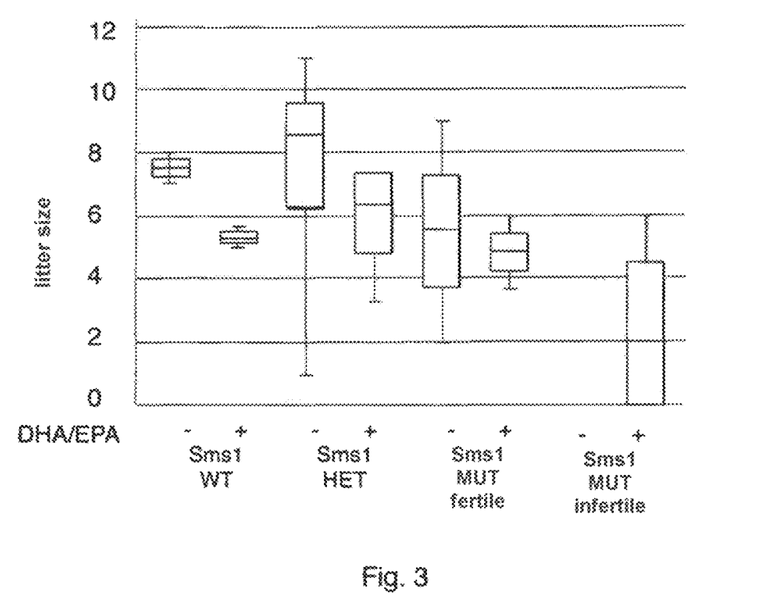
Figure 4:
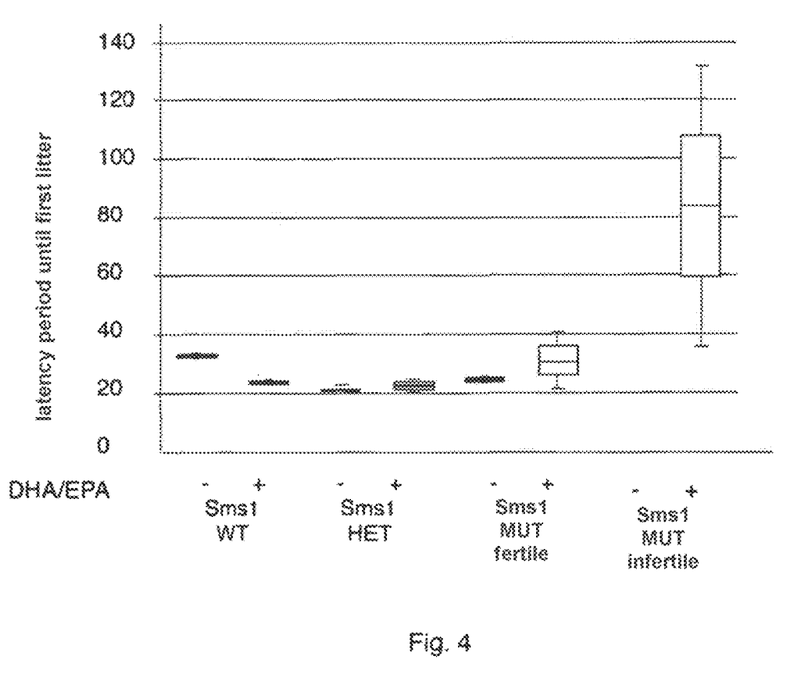

As FIG. 3 shows, the genetically manipulated and at first infertile mice have become fertile through the intake of the mixture. From FIG. 4, which shows the time to litter after mating, it is clear that wild type mice (WT), heterozygotic (HET) and fertile genetically manipulated mice (MUT) with feeding with the agent also needed a similarly long time until the first litter. In contrast to this, the infertile and genetically manipulated mice fed with said mixture and thereby cured of the infertility needed markedly more time.

Figure 5:
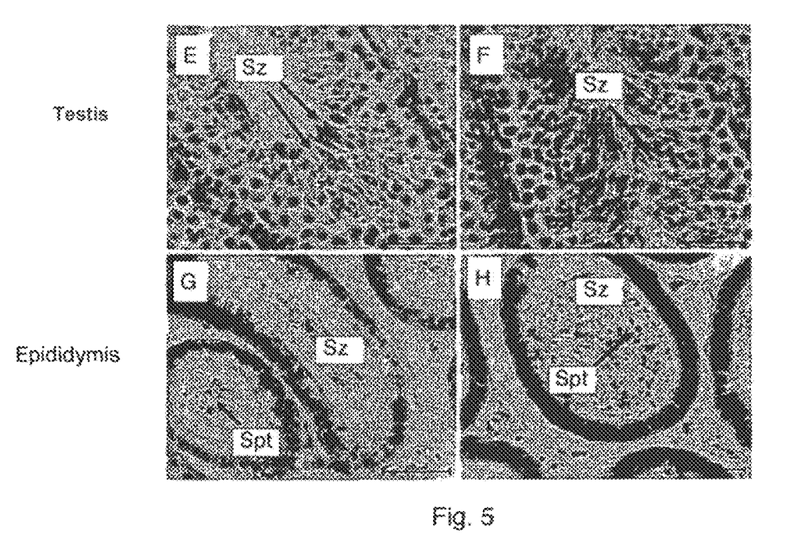

Further, as is clear from FIG. 5, the enrichment of the normal diet with DHA and EPA led to an improvement in the testicular pathology of the genetically manipulated mice. Previously infertile genetically manipulated mice, which had produced progeny after the DHA/EPA treatment, showed markedly slighter pathological changes in the testes (see FIG. 4E and FIG. 4F) and also in the epididymides (see FIG. 4G and FIG. 4H) in comparison to the wild type mice. Arrows in FIG. 4 point to elongated spermatids (Spt) and spermatozoa (Sz). As can be discerned, the spermatozoa dominate over the spermatids. This is consistent with the maturation cycle for sperms and a reduction in the testicular pathology.

The invention claimed is:

1. A method for treating a human or animal having an impaired sphingolipid metabolism, the method comprising administering to the human or animal an effective amount of an omega-3 and/or omega-6 fatty add or an ester or a salt thereof, wherein the treatment is for Niemann-Pick disease, Tay-Sachs disease, Sandhoff disease, Tay-Sachs AB variant, Gaucher disease, Fabry disease, Krabbe disease, GM1 gangliosidosis, metachromatic leukodystrophy or fucosidosis.

2. The method according to claim 1, wherein the impaired sphingolipid metabolism is due to impaired sphingolipid synthesis and/or excessive sphingolipid degradation.

3. The method according to claim 1, wherein the impaired sphingolipid metabolism is due to a deficient, reduced and/or defective formation of sphingomyelin synthase 1 enzyme or sphingomyelin synthase 2 enzyme.

4. The method according to claim 1, wherein the impaired sphingolipid metabolism is due to a deficient sphingolipid content in blood and/or in a testis.

5. The method according to claim 1, wherein the impaired sphingolipid metabolism is due to a defect in the sphingomyelin synthase 1 gene and/or in the sphingomyelin synthase 2 gene.

6. The method according to claim 1, wherein the omega-3 and/or omega-6 fatty acid comprises a multiply unsaturated omega-3 and/or omega-6 fatty acid.

7. The method according to claim 6, wherein the omega-3 and/or omega-6 fatty acid comprises EPA, DHA, DPA, ETA, 21:5n3 and/or SDA.

8. The method according to claim 1, wherein the omega-3 and/or omega-6 fatty acids are used as free fatty acids or in bound form.

9. The method according to claim 1, wherein the omega-3 and/or omega-6 fatty acid are administered in a dosage of more than 0.5 g/day.

10. The method according to claim 1, wherein the omega-3 and/or omega-6 fatty acid are administered in a dosage of 1 to 3 g/day.

11. The method according to claim 1, wherein the treatment is for Niemann-Pick disease.

12. The method according to claim 1, wherein the treatment is for Tay-Sachs disease.

13. The method according to claim 1, wherein the treatment is for Sandhoff disease.

14. The method according to claim 1, wherein the treatment is for Tay-Sachs AB variant.

15. The method according to claim 1, wherein the treatment is for Gaucher disease.

16. The method according to claim 1, wherein the treatment is for Fabry disease.

17. The method according to claim 1, wherein the treatment is for Krabbe disease.

18. The method according to claim 1, wherein the treatment is for GM1 gangliosidosis.

19. The method according to claim 1, wherein the treatment is for metachromatic leukodystrophy.

20. The method according to claim 1, wherein the treatment is for fucosidosis.

* * * * *

UNITED STATES PATENT AND TRADEMARK OFFICE
CERTIFICATE OF CORRECTION

PATENT NO. : 10,744,108 B2  
APPLICATION NO. : 15/735749  
DATED : August 18, 2020  
INVENTOR(S) : Thomas Hartmann et al.

Page 1 of 1

It is certified that error appears in the above-identified patent and that said Letters Patent is hereby corrected as shown below:

Column 7 Line 14 Claim 1 should read:
The invention claimed is:
1. A method for treating a human or animal having an impaired sphingolipid metabolism, the method comprising administering to the human or animal an effective amount of an omega-3 and/or omega-6 fatty acid or an ester or a salt thereof, wherein the treatment is for Niemann-Pick disease, Tay-Sachs disease, Sandhoff disease, Tay-Sachs AB variant, Gaucher disease, Fabry disease, Krabbe disease, GM1 gangliosidosis, metachromatic leukodystrophy or fucosidosis.

Signed and Sealed this
First Day of December, 2020

Andrei Iancu
*Director of the United States Patent and Trademark Office*